| United States Patent [19] | [11] | 4,304,679 |
|---|---|---|
| Hooper et al. | [45] | Dec. 8, 1981 |

[54] DETERGENT PRODUCT CONTAINING DEODORANT COMPOSITIONS

[75] Inventors: David C. Hooper, Ashford; George A. Johnson; Donald Peter, both of Wirral, all of England

[73] Assignee: Lever Brothers Company, New York, N.Y.

[21] Appl. No.: 933,932

[22] Filed: Aug. 15, 1978

[30] Foreign Application Priority Data

Jan. 12, 1978 [GB] United Kingdom ................. 1286/78

[51] Int. Cl.$^3$ .......................... C11D 3/48; C11D 3/50
[52] U.S. Cl. .................................... 252/106; 252/107; 252/108; 252/132; 252/135; 252/174.11
[58] Field of Search ............... 252/89 R, 99, 106, 135, 252/132, 546, 547, 558, 559, 174.11

[56] References Cited

U.S. PATENT DOCUMENTS

| | | |
|---|---|---|
| 2,875,131 | 2/1959 | Carpenter et al. ............... 252/522 X |
| 2,889,254 | 6/1959 | Fiore et al. ....................... 252/522 X |
| 2,976,321 | 3/1961 | Dorsky et al. ................... 252/522 X |
| 3,144,467 | 8/1964 | Houlihan ........................... 260/343.2 |
| 3,268,594 | 8/1966 | Bedoukian ........................... 260/615 |
| 3,317,397 | 5/1967 | Saunders ......................... 252/108 X |
| 3,318,945 | 5/1967 | Erman ................................. 260/468 |
| 3,493,650 | 2/1970 | Dunkel ................................. 424/65 |
| 3,591,643 | 7/1971 | Fanta et al. ....................... 260/617 F |
| 3,662,007 | 5/1972 | Fanta et al. ....................... 260/631.5 |
| 3,679,756 | 7/1972 | Kretschmar et al. ............. 260/631.5 |
| 3,684,723 | 8/1972 | Best et al. ............................. 252/132 |
| 3,836,232 | 10/1974 | Ohloff et al. ......................... 252/522 |
| 3,862,049 | 1/1975 | McGarth et al. ..................... 252/108 |
| 3,969,259 | 7/1976 | Lages ................................... 252/107 |
| 4,055,506 | 10/1977 | Pittet et al. ........................... 252/132 |
| 4,066,710 | 1/1978 | Ochsner ............................ 260/631.5 |
| 4,100,110 | 7/1978 | Ansari et al. ......................... 252/522 |
| 4,129,569 | 12/1978 | Schreiber et al. ............. 260/307 FA |

FOREIGN PATENT DOCUMENTS

| | | |
|---|---|---|
| 7604601 | 8/1977 | Brazil . |
| 2440025 | 3/1975 | Fed. Rep. of Germany . |
| 2454969 | 5/1975 | Fed. Rep. of Germany . |
| 2461593 | 7/1975 | Fed. Rep. of Germany . |
| 2502767 | 7/1975 | Fed. Rep. of Germany . |
| 2461605 | 10/1975 | Fed. Rep. of Germany . |
| 2516696 | 10/1975 | Fed. Rep. of Germany . |
| 2535576 | 2/1976 | Fed. Rep. of Germany . |
| 2540624 | 4/1976 | Fed. Rep. of Germany . |
| 2455761 | 6/1976 | Fed. Rep. of Germany . |
| 858826 | 1/1961 | United Kingdom . |
| 1085940 | 10/1967 | United Kingdom . |
| 1197817 | 7/1970 | United Kingdom . |
| 1266060 | 3/1972 | United Kingdom . |
| 1282889 | 7/1972 | United Kingdom . |
| 1302933 | 1/1973 | United Kingdom . |
| 1359492 | 7/1974 | United Kingdom . |
| 1420949 | 1/1976 | United Kingdom . |

OTHER PUBLICATIONS

"Handbuch der Kosmetika and Ricchstoffe, Band 2," H. Janistyn, 1969.
"Handbuch der Gesamten Perfumerie and Kosmetik," Fred Winter, 1952, pp. 735-754.
Sagarin, "Cosmetics-Science & Technology" (M. S. Balsam) Chapter 32, 1972, pp. 599 and 608-621.

*Primary Examiner*—P. E. Willis, Jr.
*Attorney, Agent, or Firm*—James J. Farrell; Melvin H. Kurtz; Irving N. Feit

[57] ABSTRACT

A deodorant detergent product comprises a non-soap detergent active compound, and a deodorant composition. The product can be used for personal washing of the skin and will as a result reduce human body malodor. The product can also be employed for washing fabrics which when subsequently worn in contact with the skin aid in the reduction of human body malodor.

14 Claims, No Drawings

DETERGENT PRODUCT CONTAINING DEODORANT COMPOSITIONS

This invention relates to deodorant detergent products for use in suppressing human body malodour.

BACKGROUND TO THE INVENTION

It has long been recognised that the development of body malodour is largely due to bacterial action on the products of the sweat glands. Washing the skin with a detergent, for instance in the form of a personal washing detergent bar, removes malodorous products and reduces the concentration of bacteria on the skin. Likewise, washing soiled clothing with a fabric washing detergent product, for instance in the form of a powder or liquid detergent product, removes malodorous products and bacteria derived from the skin.

It has been customary to incorporate germicides into detergent products, particularly those designed for personal washing, in the belief that growth of those skin microflora that contribute to body malodour can be inhibited and the production of malodorous substances suppressed. Germicides are at least partly effective in reducing or retarding the development of body malodour, but they do not completely solve the problem, possibly because there are other causes of malodour development on the skin which are unrelated to the proliferation of bacteria.

SUMMARY OF THE INVENTION

It has now been discovered that certain combinations of materials other than germicides, hereinafter referred to as "deodorant compositions", when incorporated into detergent products for personal washing provide a more effective means for inhibiting malodour development on the skin than the use of the conventional germicides. Likewise, it has also been discovered that deodorant compositions, when incorporated into a fabric washing detergent product, can be deposited onto the fabric of a garment washed with the product, so that the fabric of the garment then has the property of reducing body malodour when the garment is subsequently worn in contact with the skin.

In the course of attempts to characterise this new principle, many hundreds of materials have been screened. Furthermore, detergent products containing hundreds of formulations made by blending materials have been examined in order to characterise the new principle.

DEFINITION OF THE INVENTION

In its widest aspect, the invention provides a deodorant detergent product comprising from 0.5 to 99.99% by weight of a non-soap detergent active compound, and from 0.01 to 10% by weight of a deodorant composition comprising from 45 to 100% by weight of deodorant components, said components having a lipoxidase-inhibiting capacity of at least 50% or a Raoult Variance Ratio of at least 1.1, said components being classified into six classes consisting of:
Class 1: phenolic substances
Class 2: essential oils, extracts, resins and synthetic oils
Class 3: aldehydes and ketones
Class 4: polycyclic compounds
Class 5: esters
Class 6: alcohols provided that where a component can be classified into more than one class it is placed in the lower or lowest numbered class; said components being selected so that:
(a) the deodorant composition contains at least five components of which at least one must be selected from each of class 1, class 2 and class 4;
(b) the deodorant composition contains components from at least 4 of the 6 classes; and
(c) any component present in the deodorant composition at a concentration of less than 0.5% by weight of said composition is eliminated from the requirements of (a) and (b).

The invention also provides a process for preparing a deodorant detergent product which process comprises blending a non-soap detergent active compound and a deodorant composition as herein defined to provide a deodorant detergent product.

The invention furthermore provides a method for suppressing human body malodour which comprises applying to the human skin in the region of apocrine sweat glands an effective amount of the deodorant detergent product as herein defined.

The invention furthermore provides a method for suppressing human body malodour which comprises contacting the skin with a fabric treated with a deodorant detergent product as herein defined.

It is a preferred property of the deodorant detergent product of the invention that it should comprise a deodorant composition which satisfies a deodorancy test when applied to the skin of human subjects. The average amount by which body malodour should be reduced is expressed in terms of the deodorant value of the deodorant composition contained in the detergent product. Products of the invention accordingly preferably comprise a deodorant composition having a deodorant value of from 0.50 to 3.5. Products in which the deodorant composition has a deodorant value of below 0.50 are outside the scope of this invention and are considered to be incapable of reducing body malodour to a significant extent.

THE DEODORANT VALUE TEST

In this test the deodorant value of a deodorant composition is measured by assessing its effectiveness, when contained in a standard soap bar at a standard concentration, in reducing body malodour when the standard soap bar is used to wash the axillae (armpits) of a panel of human subjects.

The choice of a soap base is not critical to the performance of the test but as illustrative of the conduct of the test in this respect the procedure followed in the preparation of the base employed in many of the tests referred to later in this specification is included in the description of the test.

Standard soap bars are prepared as follows, all amounts given being by weight.

As soap base there is used a neutral wet sodium soap containing 63% of total fatty matter of which 82% is tallow fatty acid and 18% is coconut oil fatty acid. To a homogeneous mixture of 9000 parts of this soap base and 340 parts of free coconut oil fatty acid at 80° C. are added with mixing, 9.4 parts of a 20% aqueous solution of tetrasodium ethylenediamine tetraacetate, 2.2 parts of a 60% aqueous solution of 1-hydroxyethane-1,1-diphosphonic acid and 7.2 parts of butylated hydroxy toluene (BHT) antioxidant dissolved in a little methylated spirits and the temperature of the mass is raised to 140° C. under superatmospheric pressure. The mass is then sprayed at about 30 mm of mercury, to produce a dried soap composition which is collected and extruded at 30° C. as noodles of about 12% moisture content.

9,770 parts of the soap noodles thus obtained are mixed at ambient temperature with 150 parts of the deodorant composition to be tested, together with 30 parts of a titanium dioxide opacifier and 50 parts of a colourant suspension. The resulting mixture is milled and plodded in conventional equipment, cut into billets and stamped into bars. The deodorant composition to be tested is therefore present at the standard level of 1.5%. These bars are described as 80/20/5 soap base and consist of 80 parts tallow soap and 20 parts coconut soap, 5 parts of this soap mixture being free fatty acids expressed as coconut oil fatty acid.

Control soap bars are prepared in a similar manner except that the deodorant composition is omitted. In other respects, the control bar should only contain those additives conventionally present in personal washing products and for the purpose in the amount conventionally used in the art. For example, it is permissible as indicated in the foregoing description to include anti-oxidants in the control bar, but these should be present only in the amount required to stabilise the soap base.

The test is conducted as follows

A team of 3 Caucasian female assessors of age within the range of from 20 to 40 years is selected for olfactory evaluation on the basis that each is able to rank correctly the odour levels of the series of aqueous isovaleric acid solutions listed in Table 1 below, and each is able to detect the reduction in body odour following application to the axillae of human subjects of soap containing 2% germicides, according to the procedure described in Whitehouse and Carter, Proc. Scientific Section of the Toilet Goods Association, 48, 31, (1967).

A panel of 50 human subjects for use in the test is assembled from Caucasian male subjects of age within the range of from 20 to 55 years. By screening, subjects are chosen who develop axilliary body malodour that is not unusually strong and who do not develop a stronger body malodour in one axilla compared with the other. Subjects who develop unusually strong body malodour, for example, due to a diet including curry or garlic, are not selected for the panel.

For two weeks before the start of a test, the panel subjects are assigned a non-deodorant soap bar for exclusive use of bathing and are denied the use of any type of deodorant or antiperspirant. At the end of this period, the 50 subjects are randomly divided into two groups of 25. The control soap bars are then applied to the left axillae of the first group and the right axillae of the second, and the test soap bars are applied to the right axillae of the first group and the left axillae of the second.

The soap bars are applied by a technician using a standard technique in which a wet flannel is soaped with the soap bar for 15 seconds, the axilla is washed with the soaped flannel for 30 seconds, then wiped with a water rinsed flannel and dried with a clean towel. Each subject then puts on a freshly laundered shirt, and 5 hours after application the odour intensity of each subject is assessed, the left axilla of each subject being assessed before the right. The application and assessment are carried out on each of four successive days.

The odour intensity is evaluated by all three assessors who, operating without knowledge of the soap bars used for each subject or the result of evaluation of their fellow-assessors, sniff each axilla and assign a score corresponding to the strength of the odour on a scale from 0 to 5, with 0 corresponding to no odour and 5 representing very strong odour. Before evaluation each subject stands with his arms against his side: he then raises one arm straight overhead, flattening the axilla vault and making it possible for the assessor's nose to be brought close to the skin, the assessor makes an evaluation and the procedure is repeated with the other axilla.

Standard aqueous solutions of isovaleric acid which correspond to each of the scores 1,2,3,4 and 5 are provided for reference to assist the assessors in the evaluation. These are shown in Table 1 below.

TABLE 1

| Score | Odour Level | Concentrations of aqueous solution of isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | 3.57 |

The scores recorded by each assessor for each soap bar are averaged and the average score of the test soap bars deducted from the average score of the control soap bars to give the deodorant value of the deodorant composition present in the test soap bars.

As a check that the selection of panel subjects is satisfactory for operation of the test, the average score with the control soap bars should be between 2.5 and 3.5.

More generally, deodorant values can be determined at other deodorant composition concentrations or with detergent products other than the standard soap bar using a test similar to the test described above. Later in this specification examples are given of solid and liquid non-soaps detergent products.

Although the invention in its widest aspect provides deodorant detergent products comprising deodorant compositions having a deodorant value of from 0.50 to 3.5, preferred deodorant detergent products are those comprising deodorant compositions which have a deodorant value of at least 0.60, or 0.70, or 0.80, or 0.90, or 1.00, or 1.20, the higher the minimum value, the more effective is the product as a deodorant detergent product as recorded by the assessors in the deodorant value test. It has also been noted that consumers, who are not trained assessors, can detect by self-assessment a noticeable reduction in body malodour where the deodorant value is at least 0.70, the higher the deodorant value above this figure, the more noticeable is the deodorant effect.

1. NON-SOAP DETERGENT ACTIVE COMPOUND

Non-soap detergent active compounds suitable for use in deodorant detergent products of the invention can be non-soap anionic or nonionic or cationic or amphoteric or Zwitterionic in character. Typical non-soap anionic detergent-active compounds include water-soluble salts, particularly the alkali metal, ammonium and alkanolammonium salts, of organic sulphuric reaction products having in their molecular structure an alkyl group containing from about 8 to about 22 carbon atoms and a sulphuric acid or sulphuric acid ester group. (Included in the term "alkyl" is the alkyl portion of acyl groups). Examples of this group of non-soap detergents which can be used are the sodium and potassium alkyl sulphates, especially those obtained by sulphating the higher alcohols ($C_8$–$C_{18}$ carbon atoms) produced by reducing the glycerides of tallow or coconut oil; and sodium and potassium alkyl benzene sulphonates, in which the alkyl group contains from about 9 to about 15 carbon atoms in straight chain or branched chain configuration.

Other non-soap anionic detergent-active compounds include the sodium alkyl glycerol ether sulphonates, especially those ethers or higher alcohols derived from tallow and coconut oil; sodium coconut oil fatty acid monoglyceride sulphonates and sulphates; and sodium or potassium salts of alkyl phenol ethylene oxide ether sulphate containing about 1 to about 10 units of ethylene oxide per molecule and wherein the alkyl groups contain about 8 to about 12 carbon atoms.

Other useful non-soap anionic detergent-active compounds include the water-soluble salts of esters of α-sulphonated fatty acids containing from about 6 to 20 carbon atoms in the ester group; water-soluble salts of 2-acyloxy-alkane-1-sulphonic acids containing from about 2 to 9 carbon atoms in the acyl group and from about 9 to about 23 carbon atoms in the alkane moiety; alkyl ether sulphates containing from about 10 to 20 carbon atoms in the alkyl group and from about 1 to 30 moles of ethylene oxide; water-soluble salts of olefin sulphonates containing from about 12 to 24 carbon atoms; and β-alkyloxy alkane sulphonates containing from about 1 to 3 carbon atoms in the alkyl group and from about 8 to 20 carbon atoms in the alkane moiety.

Preferred water-soluble non-soap anionic detergent-active compounds include linear alkyl benzene sulphonates containing from about 11 to 14 carbon atoms in the alkyl group: the tallow range ($C_{12-20}$) alkyl sulphates; the coconut range alkyl glyceryl sulphonates; and alkyl ether sulphates wherein the alkyl moiety contains from about 14 to 18 carbon atoms and wherein the average degree of ethoxylation varies between 1 and 6.

Specific preferred non-soap anionic detergent-active compounds include: sodium linear $C_{10}$–$C_{12}$ alkyl benzene sulphonate triethanolamine $C_{10}$–$C_{12}$ alkyl benzene sulphonate; sodium tallow alkylsulphate; and sodium coconut alkyl glyceryl ether sulphonate; and the sodium salt of a sulphated condensation product of tallow alcohol with from about 3 to about 10 moles of ethylene oxide.

It is to be understood that any of the foregoing anionic detergent-active compounds can be used separately or as mixtures.

Examples of suitable nonionic detergent-active compounds are condensates of linear and branched chain aliphatic alcohols or carboxylic acids of from 8 to 18 carbon atoms with ethylene oxide, for instance a coconut alcohol-ethylene oxide condensate of 6 to 30 moles of ethylene oxide per mole of coconut alcohol; condensates of alkylphenols whose alkyl group contains from 6 to 12 carbon atoms with 5 to 25 moles of ethylene oxide per mole of alkylphenol; condensates of the reaction product of ethylenediamine and propylene oxide with ethylene oxide, the condensates containing from 40 to 80% of polyoxyethylene radicals by weight and having a molecular weight of from 5,000 to 11,000; tertiary amine oxides of structure $R_3NO$, where one group R is an alkyl group of 8 to 18 carbon atoms and the others are each methyl, ethyl or hydroxyethyl groups, for instance dimethyldodecylamine oxide; tertiary phosphine oxides of structure $R_3PO$, where one group R is an alkyl group of from 10 to 18 carbon atoms, and the others are each alkyl or hydroxyalkyl groups of 1 to 3 carbon atoms, for instance dimethyldodecylphosphine oxide; and dialkyl sulphoxides of structure $R_2SO$ where the group R is an alkyl group of from 10 to 18 carbon atoms and the other is methyl or ethyl, for instance methyltetradecyl sulphoxide.

Suitable cationic detergent-active compounds are quaternary ammonium salts having an aliphatic radical of from 8 to 18 carbon atoms, for instance cetyltrimethyl ammonium bromide.

Examples of suitable amphoteric detergent-active compounds are derivatives of aliphatic secondary and tertiary amines containing an alkyl group of 8 to 18 carbon atoms and an aliphatic radical substituted by an anionic water-solubilising group, for instance sodium 3-dodecylaminopropionate, sodium 3-dodecylaminopropane sulphonate and sodium N-2-hydroxydodecyl-N-methyltaurate.

Suitable zwitterionic detergent-active compounds are derivatives of aliphatic quaternary ammonium, sulphonium and phosphonium compounds having an aliphatic radical of from 8 to 18 carbon atoms and an aliphatic radical substituted by an anionic water-solubilising group, for instance 3-(N,N-dimethyl-N-hexadecylammonium)propane-1-sulphonate betaine, 3-(dodecylmethyl sulphonium)propane-1-sulphonate betaine and 3-(cetylmethylphosphonium)ethane sulphonate betaine.

In addition to any of the above non-soap detergent-active compounds, soaps can optionally also be present. Soaps are salts of fatty acids and include alkali metal soaps such as the sodium, potassium, ammonium and alkanol ammonium salts of higher fatty acids containing from about 8 to about 24 carbon atoms, and preferably from about 10 to about 20 carbon atoms. Particularly useful are the sodium and potassium and mono-, di- and triethanolamine salts of the mixtures of fatty acids derived from coconut oil and tallow.

Further examples of detergent-active compounds are compounds commonly used as surface-active agents given in the well-known textbooks "Surface Active Agents", Volume 1 by Schwartz and Perry and "Surface Active Agents and Detergents", Volume II by Schwartz, Perry and Berch.

The amount of non-soap detergent-active compound that can be incorporated into deodorant detergent products according to the invention is from 0.5 to 99.99% by weight. The preferred amount will depend on the nature of the product (i.e. whether it is liquid or solid and whether it comprises only non-soap detergents or both soap and non-soap detergents).

It can be stated generally that the preferred amount of non-soap detergent active compound to be employed for solid products is within the range of from 5 to 95% by weight and for liquid products is within the range of from 5 to 80% by weight.

2. THE DEODORANT COMPOSITION

The characterisation of the deodorant composition of the invention presents difficulties, since it cannot be defined solely in terms of substances of specified structure and combinations in specified proportions. Nevertheless, procedures have been discovered that enable the essential materials of the deodorant compositions to be identified by tests.

The essential materials required for the formulation of deodorant compositions are those having a lipoxidase-inhibiting capacity of at least 50% or those having a Raoult variance ratio of at least 1.1, as determined by the following tests, which are designated the lipoxidase and morpholine tests respectively.

THE LIPOXIDASE TEST

In this test the capacity of a material to inhibit the oxidation of linoleic acid by lipoxidase (EC1.13.1.13) to form a hydroperoxide is measured.

Aqueous 0.2 M sodium borate solution (pH 9.0) is used as buffer solution.

A control substrate solution is prepared by dissolving linoleic acid (2.0 ml) in absolute ethanol (60 ml), diluting with distilled water to 100 ml and then adding borate buffer (100 ml) and absolute ethanol (300 ml).

A test substrate solution is prepared in the same way as the control substrate solution except that for the absolute ethanol (300 ml) is substituted the same volume of a 0.5% by by weight solution in ethanol of the material to be tested.

A solution of the enzyme lipxodase in the borate buffer and having an activity within the range of from 15,000 to 40,000 units per ml is prepared.

The activity of the lipxodiase in catalysing the oxidation of linoleic acid is first assayed spectrophotometrically using the control. An automatic continuously recording spectrophotometer is used and the increase in extinction at 234 nm (the peak of hydroperoxide) is measured to follow the course of oxidation, the enzyme concentration used being such that it gives an increase in optical density ($\Delta OD$) at 234 nm within the range of from 0.6 to 1.0 units per minute. The following ingredients are placed in two 3 ml cuvettes:

|  | Control (ml) | Blank (ml) |
| --- | --- | --- |
| Control substrate solution | 0.10 | 0.10 |
| Absolute ethanol | 0.10 | 0.10 |
| Borate buffer | 2.75 | 2.80 |
| Lipoxidase solution | 0.05 |  |

The lipoxidase solution is added to the control cuvette last and the reaction immediately followed spectrophotometrically for about 3 minutes, with recording of the increase in optical density at 234 nm as a curve on a graph.

The capacity of a material to inhibit the oxidation is then measured using a test sample containing enzyme, substrate and a deodorant material. The following ingredients are placed in two 3 ml cuvettes.

|  | Test Sample (ml) | Blank (ml) |
| --- | --- | --- |
| Test substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the test sample cuvette last and the course of the reaction immediately followed as before.

The lipoxidase-inhibiting capacity of the material is then calculated from the formula $100(S_1-S_2)/S_1$, where $S_1$ is the slope of the curve obtained with the control and $S_2$ is the slope of the curve obtained with the test sample, and thus expressed as % inhibition. A material that gives at least 50% inhibition in the test is hereafter referred to as having a lipoxidase-inhibiting capacity of at least 50%.

THE MORPHOLINE TEST

In this test the capacity of a material to depress the partial vapour pressure of morpholine more than that required by Raoult's Law is measured. Substances that undergo chemical reaction with morpholine, for examle aldehydes, are to be regarded as excluded from the test.

Into a sample bottle of capacity 20 ml is introduced morpholine (1 g) the bottle fitted with a serum cap and then maintained at 37° C. for 30 minutes for equilibrium to be reached. The gas in the headspace of the bottle is analysed by piercing the serum cap with a capillary needle through which nitrogen at 37° C. is passed to increase the pressure in the bottle by a standard amount and then allowing the excess pressure to inject a sample from the headspace into gas chromatograph apparatus, which analyses it and provides a chromatographic trace curve with a peak due to morpholine, the area under which is proportional to the amount of morpholine in the sample.

The procedure is repeated under exactly the same conditions using instead of morpholine alone, morpholine (0.25 g) and the material to be tested (1 g); and also using the material (1 g) without the morpholine to check whether it gives an interference with the morpholine peak (which is unusual).

The procedure is repeated until reproducible results are obtained. The areas under the morpholine peaks are measured and any necessary correction due to interference by the material is made.

A suitable apparatus for carrying out the above procedure is a Perkin-Elmer Automatic GC Multifract F40 for Head Space Analysis. Further details of this method are described by Kolb in "CZ-Chemie-Technik", Vol 1, No 2, 87–91 (1972) and by Jentzsch et al in "Z. Anal. Chem." 236, 96–118 (1968).

The measured areas representing the morpholine concentration are proportional to the partial vapour pressure of the morpholine in the bottle headspace. If A is the area under the morpholine peak when only morpholine is tested and A' is the area due to morpholine when a material is present, the relative lowering of partial vapour pressure of morpholine by the material is given by $1 - A'/A$.

According to Raoult's Law, if at a given temperature the partial vapour pressure of morpholine in equilibrium with air above liquid morpholine is p, the partial vapour pressure p' exerted by morpholine in a homogeneous liquid mixture of morpholine and material at the same temperature is $pM/(M+PC)$, where M and PC are the molar concentrations of morpholine and material. Hence, according to Raoult's Law the relative lowering of morpholine partial vapour pressure (p-p')/p, is given by $1-M/(M+PC)$, which under the circumstances of the test is $87/(87+m/4)$, where m is the molecular weight of the perfume material.

The extent to which the behaviour of the mixture departs from Raoult's Law is given by the ratio $$\frac{1 - A'/A}{87/(87 + m/4)}$$

The above ratio, which will be referred to as the Raoult variance ratio, is calculated from the test results. Where a material is a mixture of compounds, a calculated or experimentally determined average molecular weight is used for m. A material that depresses the partial vapour pressure of morpholine by at least 10% more than that required by Raoult's Law is one in which the Raoult variance ratio is at least 1.1.

A large number of materials which satisfy one or both tests is described later in this specification and these are hereafter referred to as "components", in contrast to other materials which fail both tests which are referred to as "ingredients".

Before defining the more detailed aspects of the invention so far as it relates to deodorant compositions, it is necessary to clarify some of the terms that will be employed.

A composition is a blend of organic compounds. For the purposes of this specification it is necessary to identify the "components" in the composition. This is done by first describing the composition in terms of four categories. These categories are given below. Examples of components in each category are provided.

(1) Single chemical compounds whether natural or synthetic, e.g. coumarin (natural or synthetic), iso-eugenol, benzyl salicylate. The majority of components are in this category.

(2) Synthetic reaction products (products of reaction), mixtures of isomers and possibly homologues, e.g. α-iso-methyl ionone.

(3) Natural oils, gums and resins, and their extracts, e.g. patchouli oil, geranium oil, clove leaf oil, benzoin resinoid.

(4) Synthetic analogues of category 3. This category includes materials that are not strict analogues of natural oils, gums and resins but are materials that result from attempts to copy or improve upon materials of category 3, e.g. Bergamot AB 430, Geranium AB 76, Pomeransol AB 314.

Components of Categories (3) and (4) although often uncharacterised chemically are available commercially.

Where a material is supplied or used conventionally for convenience as a mixture, e.g. p-t-Amylcyclohexanone diluted with diethyl phthalate, for the purposes of this specification two components are present, so that use of 5% of a blend of 1 part of this ketone and 9 parts of diethyl phthalate is represented as 0.5% of the ketone and 4.5% of diethyl phthalate.

It has been found advantageous in formulating the most effective deodorant composition for incorporation into the detergent product of the invention to use components that, as well as satisfying the lipoxidase or morpholine tests, satisfy further conditions. These conditions are:

(i) there must be at least five components present,
(ii) each of these components must be selected from at least four different chemical classes (to be defined below),
(iii) a component from each of classes 1, 2 and 4 must be present,
(iv) at least 45%, preferably at least 50 and most preferably from 60 to 100%, by weight of the deodorant composition must comprise components,
(v) a component is not considered to contribute to the efficacy of the deodorant composition if it is present in the deodorant composition at a concentration of less than 0.5% by weight, and
(vi) a class is not considered to contribute to the efficacy of the deodorant composition if it is present in the deodorant composition at a concentration of less than 0.5% by weight.

Therefore, according to a preferred embodiment of the invention, there is provided a deodorant detergent product as herein defined in which the deodorant composition consists essentially of from about 45 to 100% by weight of at least five components and from 0 to about 55% by weight of ingredients, each of the components being selected from components having a lipoxidase inhibiting capacity of at least 50% and components having a Raoult variance ratio of at least 1.1, the components and ingredients being so chosen that the deodorant value of the deodorant composition is within the range of 0.50 to 3.5.

Each component should be allocated to one of six classes. These classes are:
Class 1—Phenolic substances
Class 2—Essential oils, extracts, resins, "synthetic" oils (denoted by "AB");
Class 3—Aldehydes and ketones;
Class 4—Polycyclic compounds;
Class 5—Esters;
Class 6—Alcohols.

In attributing a component to a class, the following rules are to be observed. Where the component could be assigned to more than one class, the component is allocated to the class occurring first in the order given above: for example clove oil, which is phenolic in character, is placed in Class 1 although it otherwise might have been allocated to Class 2. Similarly, 2-n-heptyl cyclopentanone which is a polycyclic ketone is attributed to Class 3 instead of Class 4.

The following are examples of deodorant components that either have a lipoxidase inhibiting capacity (LIC) of at least 50% or have a Raoult variance ratio (RVR) of at least 1.1. Their class, molecular weight (m), LIC and RVR as determined by the tests already described herein are also listed.

The nomenclature adopted for the components listed below and for the ingredients which appear in the deodorant formulations of the Examples is, so far as is possible, that employed by Steffen Arctander in "Perfume and Flavour Chemicals (Aroma Chemicals)" Volume I and II (1969) and the "Perfume & Flavour Materials of Natural Origin" (1960) by the same author. Where a component or other ingredient is not described by Arctander, then either the chemical name is given or, where this is not known (such as is the case with perfumery house specialities), then the supplier's identity can be established by reference to the appendix which appears at the end of the specification.

|  | LIC | RVR | m |
|---|---|---|---|
| Class 1 - Phenolic Substances | | | |
| iso-Amyl salicylate | 95 | 1.24 | 208 |
| Benzyl salicylate | 0 | 1.58 | 228 |
| Carvacrol | 32 | 1.43 | 150 |
| Clove leaf oil | 79 | 1.43 | 164 |
| Ethyl vanillin | 100 | 1.43 | 152 |
| iso-Eugenol | 100 | 1.48 | 164 |
| LRG 201 | 100 | 1.21 | 196 |
| Mousse de chene Yugo | 98 | 1.29 | 182 |
| Pimento leaf oil | 100 | — | 165 |
| Thyme oil red | 55 | 1.37 | 150 |
| Class 2 - Essential oils, extracts, resins, "synthetic" oils, (denoted by "AB") | | | |
| Benzoin Siam resinoids | 87 | — | — |
| Bergamot AB 37 | 58 | 0.97 | 175 |
| Bergamot AB 430 | 58 | 0.97 | 175 |
| Geranium AB 76 | 26 | 1.29 | 154 |
| Geranium oil | 26 | 1.29 | 154 |

-continued

|  | LIC | RVR | m |
|---|---|---|---|
| Opoponax resinoid | 96 | 1.33 | 150 |
| Patchouli oil | 76 | 1.25 | 140 |
| Petitgrain oil | 34 | 1.27 | 175 |
| Pomeransol AB 314 | 100 | — | — |
| Class 3 - Aldehydes and Ketones | | | |
| 6-Acetyl-1,1,3,4,4,6-hexamethyl-tetrahydronaphthalene | 100 | 1.03 | 258 |
| p-t-Amyl cyclohexanone | 50 | 1.10 | 182 |
| p-t-Butyl-α-methyl hydrocinnamic aldehyde | 74 | — | 204 |
| 2-n-Heptylcyclopentanone | 56 | 1.05 | 182 |
| α-iso-Methyl ionone | 100 | 1.13 | 206 |
| β-Methyl naphthyl ketone | 100 | 0.96 | 170 |
| Class 4 - Polycyclic Compounds | | | |
| Coumarin | 58 | 1.22 | 146 |
| 1,3,4,6,7,8-Hexahydro-4,6,6,7,8,8-hexamethyl cyclopenta-γ-2-benzopyran | 100 | — | 240 |
| 3a-Methyl-dodecahydro-6,6,9a-trimethylnaphtho(2,1-b)furan | 58 | 1.30 | 230 |
| β-Naphthyl methyl ether | 100 | — | 158 |
| Class 5 - Esters | | | |
| o-t-Butylcyclohexyl acetate | 52 | 1.08 | 198 |
| p-t-Butylcyclohexyl acetate | 54 | 0.98 | 198 |
| Diethyl phthalate | 79 | 1.20 | 222 |
| Nonanediol-1,3-diacetate | 33 | 1.17 | 244 |
| Nonanolide-1:4 | 92 | 0.87 | 156 |
| i-Nonyl acetate | 50 | 0.83 | 186 |
| i-Nonyl formate | 19 | 1.49 | 172 |
| Class 6 - Alcohols | | | |
| Dimyrcetol | 16 | 1.22 | 156 |
| Phenylethyl alcohol | 22 | 1.24 | 122 |
| Tetrahydromuguol | 24 | 1.23 | 158 |

It has been shown that for best results, a certain minimum average concentration of components should be present. This minimum concentration is a function of the number of classes present-the more classes present, the lower the minimum concentration. The minimum average concentration in the various situations that can apply is shown in the Table below:

| Number of classes represented in deodorant composition | Average concentration of components | |
|---|---|---|
| | minimum not less than (%) | preferably not less than (%) |
| 4 | 5 | 6 |
| 5 | 4.5 | 5.5 |
| 6 | 4.5 | 5 |

Also, it is preferred that at least 1% of each of four classes is present in the deodorant composition, but individual components which are present at a concentration of less than 0.5% are eliminated from this calculation, as is the class into which they fall if there is present no component at a concentration of at least 0.5% which falls within that class.

More specifically, the invention also provides a deodorant detergent product as herein defined wherein the amount of deodorant components in the deodorant composition present in the classes 1,2 and 4 as herein defined is at least 1%, most preferably at least 3% by weight of the deodorant composition for each class, and the amount of components present in each of at least two other classes is at least 1% by weight of the composition, provided also that any component that is present in the deodorant composition at a concentration of less than a threshold value of 0.5% by weight is eliminated from the calculation of the amounts of components in each class.

Although at least four different classes of components should preferably be represented in the deodorant composition, superior compositions can be obtained if more than four classes are represented. Accordingly, five or six classes can be represented in the deodorant composition.

It has been shown by the preparation, examination and testing of many hundreds of deodorant compositions that the best results are obtained by keeping within the aforementioned rules when selecting types and amounts of components and ingredients. For example, deodorant compositions which contain less than the minimum concentration of components of 45% are unlikely to result in a deodorant composition having a deodorant value of at least 0.50. Therefore, in preparing the best deodorant compositions of the invention, the rules for selection of components according to their classification, the representation of different classes, the amounts of each component present, bearing in mind the threshold value below which it is believed a component will not significantly contribute, are all important to observe if the best results are to be obtained.

It should be explained that components present in the deodorant detergent product for purposes other than obtaining deodorant effects, for example an adjunct like the anti-oxidant, are excluded from the operation of the preceding instructions to the extent that the component is required for that other purpose. The levels at which adjuncts are conventionally present in detergent products is well-established for established materials and readily determinable for new materials so that the application of the above exclusion presents no difficulty.

Deodorant compositions can be incorporated in deodorant detergent products according to the invention, at a concentration of from about 0.01 to about 10%, preferably from 0.5 to 5% and most preferably from 1 to 3% by weight.

It is apparent that if less than 0.01% of a deodorant composition is employed, then use of the detergent product is unlikely to provide a significant reduction in body malodour intensity. If more than 10% of a deodorant composition is employed, then use of the detergent product is unlikely to further reduce body malodour intensity beyond that observed at the 10% level.

3. DETERGENT ADJUNCTS

Deodorant detergent products of the invention can contain other detergent composition ingredients (adjuncts), for instance sequestrants, builders, soil release agents, anti-redeposition agents, superfatting agents such as free long-chain fatty acids, lather boosters such as coconut monoethanolamide; lather controllers; inorganic salts such as sodium and magnesium sulphates; moisturisers; plasticisers and thickeners; opacifiers, colourants, fluorescers, bleaching agents, perfumes, germicides, and other deodorant materials such as zinc ricinoleate. The product can also contain water.

The total amount of detergent adjuncts that can be incorporated into the deodorant detergent product according to the invention will normally form the balance of the product after accounting for the detergent composition and the detergent-active compound. The detergent adjuncts will accordingly form from 0 to 99.49L % by weight of the product.

PRODUCT TYPES AND FORMULATIONS

The deodorant product can be formulated as a solid product, for example in the form of a bar such as a personal washing bar or laundry bar, or a powder which can be used for personal washing or for fabric washing.

Alternatively, the product can take the form of a liquid product for use in personal or fabric washing or for use as a shampoo or foam bath product.

As a further alternative, the composition can take the form of a gelled product for use in personal washing, for example as a shower gel, or for fabric washing.

It is to be understood that the foregoing products are examples of forms which the deodorant detergent product can take: other product forms within the purview of the art are to be included within the scope of monopoly claimed.

The invention is further illustrated by the following examples of detergent product formulations which can be used as a basis for incorporating deodorant compositions at a concentration of from 0.01 to 10% by weight to form deodorant detergent products according to the invention.

Examples of the deodorant bars containing non-soap detergents which can be employed as a basis for incorporation of a deodorant perfume to provide deodorant detergent products according to the invention are as follows:

| Detergent bar A | % w/w |
|---|---|
| Sodium acylisethionate | 48.6 |
| Sodium dodecylbenzene sulphonate | 2.0 |
| Sodium soap | 11.0 |
| Coconut oil fatty acid | 3.0 |
| Stearic acid | 21.7 |
| Other ingredients including inorganic salts, titanium dioxide, colouring matter | 8.5 |
| Water | to 100 |

| Detergent bar B | % w/w |
|---|---|
| Sodium $C_{11}$-$C_{14}$ alkane sulphonate | 22.1 |
| Sodium $C_{15}$-$C_{18}$ alkane sulphonate | 29.4 |
| Sodium $C_{16}$-$C_{18}$ olefin sulphonate | 22.1 |
| Myristyl alcohol | 6.3 |
| Cetyl alcohol | 5.0 |
| Stearyl alcohol | 5.0 |
| Other ingredients including inorganic salts, titanium dioxide, colouring matter | 5.2 |
| Water | to 100 |

| Detergent bar C | % w/w |
|---|---|
| Disodium salt of a sulphonated hardened tallow fatty acid | 27.6 |
| Disodium salt of a sulphonated coconut oil fatty acid | 14.6 |
| Sodium $C_{11}$-$C_{15}$ alkyl sulphate | 28.1 |
| Myristyl alcohol | 11.1 |
| Other ingredients including inorganic salts, titanium dioxide, colouring matter | 7.3 |
| Water | to 100 |

An example of a liquid product which can be employed as a basis for incorporation of a deodorant composition to provide a deodorant detergent product according to the invention is as follows:

| Liquid detergent product | % w/w |
|---|---|
| Sodium lauryl ether sulphate (28% AD) | 30.0 |
| Sodium N-lauroyl sarcosinate (97% AD) | 4.0 |
| Sodium lauryl polyglycol ether oxyacetic acid | 4.0 |
| Stearic acid polyglycol ester | 2.0 |
| Polyethylene glycol 400 | 1.0 |
| Cetyl alcohol | 1.0 |
| Vinyl pyrrolidone/styrene copolymer | 3.0 |

| Liquid detergent product | % w/w |
|---|---|
| Water | to 100 |

Examples of foam bath products which can be employed as a basis for incorporation of a deodorant composition to provide deodorant detergent products according to the invention are as follows:

| Foam bath A | % w/w |
|---|---|
| Diethylamine and monobutylethanolamine salt of lauryl ether sulphate ($C_{12}$:$C_{14}$ = 70:30, 2,2$\overline{EO}$) 100% AD | 20 |
| Monolaurin | 5 |
| Ethoxylated (5$\overline{EO}$) copra monoethanolamide | 3 |
| Colour, water | to 100 |

| Foam Bath B | % w/w |
|---|---|
| Sodium lauryl ether sulphate (28% AD) | 54 |
| Monolaurin | 5 |
| A mixture of ethoxylated (8 to 10 $\overline{EO}$) $C_8$-$C_{12}$ glycerides | 6 |
| Carbitol | 3 |
| Colour, water | to 100 |

| Foam bath C | % w/w |
|---|---|
| Triethanolamine salt of lauryl sulphate (42% AD) | 24 |
| Diethylamine and monobutylethanolamine salt of lauryl ether sulphate ($C_{12}$:$C_{14}$ = 70:30, 2.2 $\overline{EO}$) 100% AD | 10 |
| Monolaurin | 5 |
| Ethoxylated (5$\overline{EO}$) copra monoethanolamide | 3 |
| Colour | 0.15 |
| Water | to 100 |

| Foam bath D | % w/w |
|---|---|
| Lauryl (poly-1-oxapropene) oxaethane carboxylic acid (100% AD) | 35 |
| Diethylamine and monobutylethanolamine salt of lauryl ether sulphate ($C_{12}$:$C_{14}$ 78/30; 2.2$\overline{EO}$) (100% AD) | 12 |
| Triglyceride $C_8$-$C_{12}$ fatty acids | 35 |
| Ethoxylated (5$\overline{EO}$) copra monoethanolamide | 8 |
| Copra diethanolamide | 5 |
| Colour | 0.5 |
| Water | to 100 |

| Foam bath E | % w/w |
|---|---|
| Lauryl (poly-1-oxapropene) oxaethane carboxylic acid (100% AD) | 35 |
| Diethylamine and monobutylethanolamine salt of lauryl ether sulphate $C_{12}$:$C_{14}$ 70:30, 2.2$\overline{EO}$) (100% AD) | 12 |
| Paraffin oil | 35 |
| Ethoxylated (5$\overline{EO}$) copra monoethanolamide | 8 |
| Copra diethanolamide | 5 |
| Colour | 0.5 |
| Water | to 100 |

| Foam bath F | % w/w |
|---|---|
| $C_{12}$-$C_{14}$ dimethylamine oxide (30% AD) | 50 |
| Lauryl(poly-1-oxapropene)oxaethane carboxylic acid (90% AD) | 5.5 |
| Polymer JR 400 | 1 |
| Ethoxylated (5$\overline{EO}$) copra monoethanolamide | 2 |

| -continued | |
|---|---|
| Colour | 0.5 |
| Water | to 100 |

| Foam bath G | % w/w |
|---|---|
| Sodium lauryl ether sulphate (3$\overline{EO}$) (28% AD) | 71.50 |
| Ethoxylated (5$\overline{EO}$) copra monoethanolamide (100% AD) | 2 |
| Polymer JR 400 | 1 |
| Colour | 0.5 |
| Water | to 100 |

| Foam bath H | % w/w |
|---|---|
| Sodium lauryl ether sulphate 3EO (28% AD) | 36 |
| $C_{12}$-$C_{14}$ dimethylamine oxide (30% AD) | 16.5 |
| Lauryl(poly-1-oxapropene)oxaethane carboxylic acid (90% AD) | 5.5 |
| Polymer JR 400 | 1 |
| Ethoxylated (5$\overline{EO}$) copra monoethanolamide (100% AD) | 2 |
| Carbitol | 3 |
| Water | to 100 |

| Foam bath I | % w/w |
|---|---|
| Lauryl(poly-1-oxapropane)oxaethane carboxylic monobutylethanolamine salt (90% AD) | 20 |
| Monolaurin | 5 |
| Ethoxylated (5$\overline{EO}$) copra monoethanolamide | 3 |
| Colour, water | to 100 |

Examples of shower gels which can be employed as a basis for incorporation of a deodorant composition to provide deodorant detergent products according to the invention are as follows:

| Shower gel A | % w/w |
|---|---|
| Triethanolamine salt of lauryl sulphate | 40 |
| Diethylamine and monobutylethanolamine salt of lauryl ether sulphate ($C_{12}$-C 70:30, 2.2$\overline{EO}$) 100% AD | 10 |
| Monolaurin | 8 |
| Colour | 0.15 |
| Water | to 100 |

| Shower gel B | % w/w |
|---|---|
| Monoethanolamine soap of $C_{12}$-$C_{18}$ fatty acids | 16.7 |
| $C_{12}$-$C_{18}$ fatty acids | 1.5 |
| Sodium acyl isethionate | 1.0 |
| Coconut diethanolamide | 3.0 |
| Glycerol | 0.5 |
| Distilled water | to 100 |

The shower gel has a pH value of 8.5–9.0 and a viscosity of 2000–6000 cps.

| Shower gel C | % w/w |
|---|---|
| Sodium myristyl lauryl ether sulphate 3$\overline{EO}$ ($C_{12}$-$C_{14}$ = 35:65) — 27% AD | 60.0 |
| Coconut diethanolamide | 2.0 |
| Formaldehyde (30%) | 0.2 |
| Sodium hexametaphosphate | 1.0 |
| Citric acid | 0.12 |
| Sodium chloride | 1.15 |
| Water, colourant | to 100 |

An example of a shampoo employed as a basis for incorporation of a deodorant composition to provide a deodorant detergent product according to the invention is as follows:

| Shampoo | % w/w |
|---|---|
| Sodium salt of triethoxylated lauryl/myristyl sulphate | 12 |
| Lauryl/myristyl dimethyl betaine | 2 |
| Coconut diethanolamide | 1 |
| Sodium chloride | 2.20 |
| Formaldehyde (40% aqueous solution) | 0.08 |
| Water | to 100 |
| pH adjusted to 7.4 with lactic acid | |

This shampoo has a viscosity of about 500 centipoise (Brookfield viscometer, spindle No 2 at 20 rpm at 25° C.). The anionic detergent consisted of about 55% lauryl and 45% myristyl materials.

Examples of fabric washing powders which can be employed as a basis for incorporation of a deodorant composition to provide a deodorant detergent product according to the invention are as follows:

| Fabric washing powder A | % w/w |
|---|---|
| Sodium $C_{13}$-$C_{18}$ alkane sulphonate | 8.0 |
| $C_{16-20}$ n-alcohol + 25 moles ethylene oxide | 3.4 |
| Sodium soap (containing 4 parts tallow fatty acid to 1 part coconut fatty acid) | 3.4 |
| Pentasodium tripolyphosphate | 37.3 |
| Sodium sulphate | 6.7 |
| Sodium carboxymethylcellulose | 2.0 |
| Ethylene diamine tetra acetic acid | 1.0 |
| Magnesium silicate | 2.0 |
| Fluorescer | 0.3 |
| Waterglass powder ($Na_2O$:$SiO_2$ = 1:3.4) | 5.9 |
| Sodium carbonate | 1.0 |
| Sodium perborate monohydrate | 19.0 |
| Water | 10.0 |

| Fabric washing powder B | % w/w |
|---|---|
| $C_{11-15}$ n-alcohol + 7 moles ethylene oxide | 12 |
| Pentasodium tripolyphosphate | 37.3 |
| Sodium sulphate | 6.7 |
| Sodium carboxymethylcellulose | 2.0 |
| Ethylenediamine tetraacetic acid | 1.0 |
| Magnesium silicate | 2.0 |
| Fluorescer | 0.3 |
| Water glass powder ($Na_2O$:$SiO_2$ = 1:34) | 5.9 |
| Sodium carbonate | 1.0 |
| Sodium perborate monohydrate | 19.0 |
| Water | to 100 |

| Fabric washing powder C | % w/w |
|---|---|
| Sodium dodecyl benzene sulphonate | 14 |
| Sodium tripolyphosphate | 40 |
| Sodium sulphate | 2 |
| Sodium carboxymethylcellulose | 1 |
| Ethylene diamine tetraacetic acid | 1 |
| Magnesium silicate | 2 |
| Fluorescer | 0.3 |
| Water glass powder ($Na_2O$:$SiO_2$ = 1:3.4) | 5.9 |
| Sodium carbonate | 1.0 |
| Sodium perborate monohydrate | 25 |
| Water | to 100 |

| Fabric washing powder D | % w/w |
|---|---|
| Sodium dodecyl benzene sulphonate | 8 |
| Tallow alcohol sulphate | 6 |
| Sodium tripolyphosphate | 40 |
| Sodium sulphate | 2 |
| Sodium carboxymethyl cellulose | 1 |
| Ethylene diamine tetraacetic acid | 1 |
| Magnesium silicate | 2 |
| Fluorescer | 0.3 |
| Water glass powder ($Na_2O$:$SiO_2$ = 1:3.4) | 5.9 |
| Sodium carbonate | 1.0 |
| Sodium perborate monohydrate | 25 |
| Water | to 100 |

| Fabric washing powder E | % w/w |
|---|---|
| Sodium dodecyl benzene sulphonate | 15 |
| Tallow alcohol 18 $\overline{EO}$ | 3 |
| Tallow alcohol 12 $\overline{EO}$ | 3 |
| Sodium stearate (soap) | 6 |
| Sodium tripolyphosphate | 40 |
| Sodium silicate | 5 |
| Sodium carboxymethylcellulose | 2 |
| Fluorescer | 0.2 |
| EDTA | 0.2 |
| Enzyme | 0.66 |
| Sodium sulphate | 14 |
| Water | to 100 |

| Fabric washing powder F | % w/w |
|---|---|
| Sodium dodecyl benzene sulphonate | 15 |
| Tallow alcohol 18 $\overline{EO}$ | 2.5 |
| Tallow alcohol 12 $\overline{EO}$ | 2.5 |
| Sodium tripolyphosphate | 30 |
| Sodium silicate | 5 |
| Sodium sulphate | 25 |
| Enzymes | 0.66 |
| EDTA | 0.2 |
| Fluorescer | 0.2 |
| Sodium carboxymethylcellulose | 2 |
| Water | to 100 |

Examples of fabric washing liquids which can be employed as a basis for incorporation of a deodorant composition to provide a deodorant detergent product according to the invention are as follows:

| Fabric washing liquid A | % w/w |
|---|---|
| Condensation product containing 7 moles ethylene oxide with a synthetic $C_{14-15}$ alcohol | 40.0 |
| Triethanolamine salt of alkyl benzene sulphonate | 19.8 |
| Triethanolamine | 5.0 |
| Ethanol | 5.0 |
| Potassium chloride | 2.5 |
| Fluorescer and colouring matter | 0.9 |
| Water | to 100 |

| Fabric washing liquid B | % w/w |
|---|---|
| Alkyl $C_{12}$ to $C_{15}$ alcohol 9 $\overline{EO}$ | 8 |
| Sodium xylene sulphonate | 2 |
| Sodium pyrophosphate | 2.8 |
| Potassium pyrophosphate | 22 |
| Sodium silicate | 3 |
| Sodium carboxymethylcellulose | 0.38 |
| Fluorescer | 0.1 |
| Water | to 100 |

An example of a detergent based deodorant cream which can be employed as a basis for incorporation of a deodorant composition to provide a deodorant detergent product according to the invention is as follows:

| Deodorant cream A | % w/w |
|---|---|
| Sodium acylisethionate (IGEPON A) - 80% AD | 10 |
| Sucrose decyl glucosidic ($C_8$-$C_{10}$ ester) (TRITON CG 110) - 70% AD | 4 |
| Monolaurin | 3 |
| Stearyl dimethylamine oxide (AMMONYX 50)- 25% AD | 1 |
| Sodium lactate (60%) | 5 |
| Bentone EW (gelling agent) | 2.5 |
| Colourant pearlescent agent | 0.25 |
| Deodorant cream A | % w/w |
| Water | to 100 |

PROCESS FOR PREPARING DEODORANT DETERGENT PRODUCTS

The process for preparing deodorant detergent products thereby employing a deodorant composition as a means for inhibiting body malodour development comprises mixing with non-soap detergent-active compounds and detergent adjuncts, if present, from 0.01 to 10% by weight of a deodorant composition to provide a deodorant detergent product, the deodorant composition preferably having a deodorant value of at least 0.50 as measured by the Deodorant Value Test. The selection of non-soap detergent active compounds and detergent adjuncts and their respective amounts employed in the process of the invention will depend upon the nature of the required detergent product (e.g. solid or liquid) and the purpose for which it is required (e.g. for personal use or for fabric washing).

Usually it is convenient to add the deodorant composition to the detergent product at a stage towards the end of its manufacture so that loss of any volatile ingredients such as may occur during a heating step is minimised.

It is furthermore usual to incorporate the deodorant composition in such a manner that it is thoroughly mixed with the other ingredients and is uniformly distributed throughout the detergent product. It is however also possible, particularly with solid products such as marbled personal washing or laundry bars and speckled or spotted solid or liquid products, where the deodorant composition can be encapsulated to delay its subsequent release, to provide detergent products where the deodorant composition is not uniformly and homogeneously mixed with the other ingredients of the detergent product, and is concentrated in the marbled bands of the speckled or spotted parts of such products.

METHOD OF USING THE DEODORANT DETERGENT PRODUCT

The deodorant detergent product of the invention is to be employed particularly for suppressing human body malodour, either by applying it directly to the skin in a personal washing mode or by laundering garments which are subsequently to be worn in contact with the skin. The deodorant detergent product is particularly effective when applied by either of these two modes of the regions of the human skin where apocrine sweat glands are most abundant, notably in the groin, axilla, anal and genital regions and in the areola of the nipple.

In use, the deodorant detergent personal washing product can for example be employed according to the procedure described herein as the Deodorant Value Test. When the product is a liquid or gel intended for personal use, for example a shower gel, the product can first be lathered on a damp cloth and then appled to the skin and finally rinsed in a washing mode.

In use, the deodorant detergent fabric washing product can for example be applied to a garment according to conventional laundering procedures involving water washing, rinsing and drying. It is apparent that sufficient of the deodorant composition is delivered to and remains on the fabric of laundered garments to subsequently enable the wearer to benefit from its deodorising effect by reduction of body malodour.

The following laundering procedure is given to illustrate the application of a deodorant detergent fabric washing product to shirts.

Polyester cotton coat style button through shirts were washed in an automatic washing machine using a nonionic detergent fabric washing powder containing as a nonionic detergent active $C_{11-15}$ n-alcohol 7EO at a concentration of 12% and a deodorant composition at a concentration of 0.2% by weight of the product. The concentration of the product in the wash liquor was 0.4% by weight of the liquor. The ratio of shirt fabric (dry weight basis) to wash liquor was 40 g fabric per liter wash liquor.

The shirts were agitated in the wash liquor for 10 minutes at a temperature of 50° C., then rinsed and spun to a moisture content of about 50% water and finally line dried to a moisture content of not greater than 10%.

The shirts were folded and stored until required for use.

SPECIFIC EXAMPLES OF THE INVENTION

The invention is illustrated by the following examples in which all parts and percentages are by weight.

EXAMPLE 1

In this example, the effect of a deodorant composition incorporated in a non-soap detergent (NSD) fabric washing powder was evaluated by the Deodorant Value Test referred to above but modified in the following manner.

Polyester cotton coat style button through shirts were first prewashed in an automatic washing machine using a nonionic detergent fabric washing powder. This was to ensure that the shirts to be used in the test were all equally clean and free from dressing prior to washing in the deodorant fabric washing product.

The washed shirts were line dried and then washed again in the automatic washing machine. The test NSD fabric washing product was then added to the wash liquor at a concentration of 0.4% by weight of the liquor. The ratio of shirt fabric (dry weight basis) to wash liquor was 40 g fabric per liter wash liquor.

The shirts were agitated in the wash liquor for 10 minutes at a temperature of 50° C., then rinsed and spun to a moisture content of about 50% water and finally line dried to a moisture content of not greater than 10%.

A further batch of prewashed shirts which were to serve as control shirts were washed again and then dried under similar conditions except that deodorant composition was omitted from the fabric washing product added to the wash liquor.

The shirts were folded and stored overnight in polyethylene bags until required for testing by a panel of male subjects and assessing for odour by a panel of female assessors.

The above procedure was repeated on four consecutive days without prewashing, half of the subjects wearing shirts treated with the deodorant composition-containing detergent product and half wearing control shirts without deodorant composition treatment.

Body odour transferred to the shirts in the region of the axillae was assessed by the trained female assessors in the manner described in the Deodorant Value Test, the odour of the shirt fabric being scored in each case rather than the axillae of the panel subjects.

The formulation of the fabric washing product was that described herein before as Fabric Washing Powder C.

Test fabric washing product was prepared by the addition of 0.2 parts of a deodorant composition to 99.8 parts of the above formulation.

The formulation of deodorant composition 1 was as follows:

| Deodorant Composition 1 | | | |
|---|---|---|---|
| Components | Parts | Class | Total in class |
| iso-Amyl salicylate | 5.0 | 1 | |
| Benzyl salicylate | 4.0 | 1 | 10.25 |
| LRG 201 | 1.25 | 1 | |
| Bergamot AB 430 | 15.0 | 2 | |
| Geranium AB 76 | 4.0 | 2 | 20.7 |
| Opoponax resinoid | 1.7 | 2 | |
| 1,3,4,6,7,8-Hexahydro-4,6,6,7,-8,8-hexamethylcyclopenta-γ-2-benzopyran | 10.0 | 4 | 10.0 |
| o-t-Butylcyclohexyl acetate | 0.5 | 5 | |
| | | | 4.25 |
| Diethyl phthalate | 3.75 | 5 | |
| Nonanolide-1,4 | 0.2* | (5) | |
| Ingredients | | | |
| Amber AB 358 | 3.0 | | |
| Benzyl alcohol | 0.15 | | |
| Cedar atlas oil | 5.0 | | |
| Citronellol | 7.0 | | |
| Citronella oil | 16.1 | | |
| Citronellyloxyacetaldehyde | 0.5 | | |
| Hexyl aldone | 0.7 | | |
| Jasmin AB 284 | 12.0 | | |
| Orange oil sweet | 8.0 | | |
| 10-Undecen-1-al | 0.15 | | |
| Vetyvert oil | 2.0 | | |
| | 100.0 | | |

*eliminated from calculation - below threshold value of 0.5%

Total amount of components 45.2
Number of components present 9
Average amount of each component 5.0
Number of classes represented 4

Results of Deodorant Value Test 1 using NSD Powder

| | Control Powder | Test Powder |
|---|---|---|
| Average scores | 2.94 | 1.97 |
| Deodorant value | | 0.97 |

By way of comparison, the Deodorant Value of the Deodorant Composition 1 was also determined in the standard 80/20/5 soap base as described in the Deodorant Value Test.

Results of Deodorant Value Test 1 using 80/20/5 soap base bar

| | Control bar | Test bar |
|---|---|---|
| Average scores | 3.46 | 2.93 |
| Deodorant value | | 0.53 |

EXAMPLE 2

In this example the effect of a deodorant composition incorporated in a non-soap detergent (NSD) personal washing bar was evaluated by the Deodorant Value Test referred to above.

Personal washing bars for use as control bars and also as a basis for incorporation of the deodorant composition had the formulation of Detergent Bar A as herein before described.

Test personal washing bars were prepared by the addition of 1.5 parts of deodorant composition of 98.5 parts of the above formulation.

The formulation of deodorant composition 2 was as follows:

| Deodorant Composition 2 | | | |
|---|---|---|---|
| Components | Parts | Class | Total in class |
| Carvacrol | 3.5 | 1 | } 4.5 |
| Thyme oil red | 1.0 | 1 | |
| Bergamot AB 37 | 20.0 | 2 | } 30.0 |
| Pomeransol AB 413 | 6.0 | 2 | |
| Petitgrain oil | 4.0 | 2 | |
| 6-Acetyl-1,1,3,4,4,6-hexa-methyl-tetrahydro-naphthalene | 3.0 | 3 | } 8.0 |
| β-Methyl naphthyl ketone | 5.0 | 3 | |
| 3a-Methyl-dodecahydro-6,6,9a-trimethyl naphtho-2(2,1-b) furan | 0.25* | (4) | |
| β-Naphthol methyl ether | 9.0 | 4 | 9.0 |
| Ingredients | | | |
| Citronellyl acetate | 5.0 | | |
| Dipropylene glycol | 4.75 | | |
| Geranyl nitrile | 1.5 | | |
| Indole | 1.0 | | |
| Lemongrass oil | 3.0 | | |
| Lime AB 402 | 10.0 | | |
| Lavendin oil | 4.0 | | |
| l-Menthol | 8.0 | | |
| Neroli AB 78 | 6.0 | | |
| Orange oil sweet | 5.0 | | |
| | 100.0 | | |

*eliminated from calculation - below threshold value of 0.5%

| | |
|---|---|
| Total amount of components | 51.5 |
| Number of components present | 8 |
| Average amount of each component | 6.4 |
| Number of classes represented | 4 |

Results of Deodorant Value Test 2 using NSD bar

| | Control bar | Test bar |
|---|---|---|
| Average scores | 3.10 | 2.10 |
| Deodorant value | | 1.00 |

By way of comparison, the Deodorant Value of Deodorant Composition 2 was also determined in the standard 80/20/5 soap base as described in the Deodorant Value Test.

Results of Deodorant Value Test 2 using 80/20/5 soap base bar

| | | |
|---|---|---|
| Average scores | 3.34 | 2.73 |
| Deodorant value | | 0.61 |

It was apparent from a comparison of these results that the effect of the deodorant composition was enhanced in the NSD bar as compared with the 80/20/5 standard soap base bar.

EXAMPLE 3

In this example the combined effect of a deodorant composition and the germicide, 2,4,4'-trichloro-2'-hydroxydiphenylether, together incorporated in a non-soap detergent (NSD) personal washing bar prepared as described in Example 2 was evaluated by the Deodorant Value Test.

Test personal washing bars were prepared by the addition of 1.5 parts of deodorant composition 3 and 0.25 parts of 2,4,4'-trichloro-2'-hydroxydiphenylether to 97.75 parts of the detergent base formulation referred to in Example 2.

The formulation of deodorant composition 3 was as follows:

| Deodorant Composition 3 | | | |
|---|---|---|---|
| Components | Parts | Class | Total in class |
| Mousse de chene Yugo | 1.25 | 1 | } 11.25 |
| Pimento leaf oil | 10.0 | 1 | |
| Benzoin Siam resinoids | 5.0 | 2 | } 25.0 |
| Bergamot AB 430 | 15.0 | 2 | |
| Geranium oil | 5.0 | 2 | |
| p-t-Amylcyclohexanone | 5.0 | 3 | } 17.0 |
| α-iso-Methyl ionone | 12.0 | 3 | |
| Coumarin | 4.0 | 4 | |
| 1,3,4,6,7,8,-Hexahydro-4,6,6,7,8,8-hexamethyl-cyclopenta-γ-2-benzopyran | 3.0 | 4 | } 7.0 |
| Diethyl phthalate | 4.35 | 5 | 4.35 |
| Ingredients | | | |
| Hercolyn D | 12.25 | | |
| Lavendin oil | 10.0 | | |
| Musk ambrette | 3.0 | | |
| Rosenta AB 380 | 10.0 | | |
| Rose-D-oxide | 0.15 | | |
| | 100.0 | | |

| | |
|---|---|
| Total amount of components | 64.6 |
| Number of components present | 10 |
| Average amount of each component | 6.5 |
| Number of classes represented | 5 |

Results of Deodorant Value Test 3 using NSD bar

| | Control bar | Test bar |
|---|---|---|
| Average scores | 3.10 | 2.16 |
| Deodorant value | | 0.94 |

By way of comparison, the Deodorant Value of the Deodorant Composition 3 was also determined in the standard 80/20/5 soap base as described in the Deodorant Value Test.

Results of Deodorant Value Test 3 using 80/20/5 soap base bar

| | Control bar | Test bar |
|---|---|---|
| Average scores | 3.04 | 2.47 |
| Deodorant value | | 0.57 |

Again, it was apparent from a comparison of these results that the effect of the deodorant composition was enhanced in the NSD bar as compared with the 80/20/5 standard soap base bar.

EXAMPLE 4

The procedure described in Example 1 was repeated using NSD Fabric Washing Powder B as hereinbefore described instead of Fabric Washing Powder C and using a different deodorant composition.

The formulation of deodorant composition 4 was as follows:

| Deodorant Composition 4 | | | |
|---|---|---|---|
| Components | Parts | Class | Total in class |
| Ethyl vanillin | 0.2* | (1) | |
| iso-Eugenol | 5.0 | 1 | } 6.25 |
| LRG 201 | 1.25 | 1 | |
| Bergamot AB 430 | 8.0 | 2 | } 15.0 |
| Patchouli oil | 7.0 | 2 | |
| 2-n-Heptylcyclopentanone | 0.5 | 3 | } 5.5 |
| α-iso-Methyl ionone | 5.0 | 3 | |
| β-Naphthol methyl ether | 7.5 | 4 | 7.5 |
| p-t-Butylcyclohexyl acetate | 4.3 | 5 | |

-continued

| Deodorant Composition 4 | | | |
|---|---|---|---|
| Diethyl phthalate | 8.25 | 5 | |
| i-Nonyl formate | 5.0 | 5 | 26.55 |
| Nonanediol-1,3-diacetate | 4.0 | 5 | |
| Phenylethyl phenyl acetate | 5.0 | 5 | |
| Tetrahydro muguol | 6.0 | 6 | 6.0 |
| Ingredients | | | |
| Citronella oil | 6.0 | | |
| Green Herbal AB 502 | 15.0 | | |
| Indole | 1.5 | | |
| Rosenta AB 380 | 6.0 | | |
| Sandalone | 4.0 | | |
| γ-Undecalactone | 0.5 | | |
| | 100.0 | | |

*eliminated from calculation - below threshold value of 0.5%

| Total amount of components | 66.8 |
|---|---|
| Number of components present | 14 |
| Average amount of each component | 4.8 |
| Number of classes represented | 6 |

Results of Deodorant Value Test 4 using NSD powder

| | Control powder | Test powder |
|---|---|---|
| Average scores | 2.69 | 1.62 |
| Deodorant value | | 1.07 |

By way of comparison, the Deodorant Value of Deodorant Composition 4 was also determined in the standard 80/20/5 soap bar as described in the Deodorant Value Test.

Results of Deodorant Value Test 4 using 80/20/5 soap base bar

| | Control bar | Test bar |
|---|---|---|
| Average scores | 3.25 | 2.10 |
| Deodorant value | | 1.15 |

EXAMPLE 5

In this example, the effect of a deodorant composition incorporated in a non-soap detergent (NSD) shower gel was evaluated by the Deodorant Value Test referred to hereinbefore in relation to a soap bar.

The formulation of the shower gel was the described hereinbefore as Shower Gel B.

Test shower gel was prepared by addition of 1.5 parts of a deodorant composition to 98.5 parts of the above formulation.

The formulation of deodorant composition 5 was as follows:

| Deodorant Composition 5 | | | |
|---|---|---|---|
| Components | Parts | Class | Total in class |
| Benzyl salicylate | 15.0 | 1 | |
| | | | 21.0 |
| Mousse de chene Yugo | 6.0 | 1 | |
| Bergamot AB 430 | 15.0 | 2 | 15.0 |
| 6-Acetyl-1,3,3,4,4,6-hexamethyl tetrahydronaphthalene | 2.5 | 3 | 2.5 |
| p-t-Amylcyclohexanone | 0.06* | (3) | |
| 3a-Methyl-dodecahydro-6,6,9a-trimethyl-naphtho-2(2,1-b) furan | 0.75 | 4 | 0.75 |
| Diethyl phthalate | 8.04 | 5 | 8.04 |
| Nonanolide-1,4 | 0.2* | (5) | |
| Dimyrcetol | 16.0 | 6 | 16.0 |
| Ingredients | | | |
| Cinnamic alcohol | 5.0 | | |
| Dimethyl benzyl carbinyl acetate | 2.5 | | |
| Dipropylene glycol | 14.25 | | |
| Geraniol | 5.0 | | |

-continued

| Deodorant Composition 5 | | |
|---|---|---|
| iso-Butyl phenyl acetate | 5.0 | |
| Methyl salicylate | 0.5 | |
| Pelargene | 4.0 | |
| Trichloromethyl phenyl carbinyl acetate | 0.2 | |
| | 100.0 | |

*eliminated from calculation - below threshold value for a component of 0.5%

| Total amount of components | 63.29 |
|---|---|
| Number of components present | 7 |
| Average amount of each component | 9.0 |
| Number of classes represented | 6 |

Results of Deodorant Value Test 5 using NSD shower gel

| | Control gel | Test gel |
|---|---|---|
| Average scores | 2.97 | 1.62 |
| Deodorant value | | 1.35 |

By way of comparison, the Deodorant Value of the Deodorant Composition 5 was also determined using the standard 80/20/5 soap base as described in the Deodorant Value Test.

Results of Deodorant Value Test 5 using 80/20/5 soap base bar

| | Control bar | Test bar |
|---|---|---|
| Average scores | 3.30 | 2.70 |
| Deodorant value | | 0.60 |

It was apparent from a comparison of these results that the effect of the deodorant composition was enhanced following use of the NSD shower gel as compared with the standard 80/20/5 soap base.

EXAMPLE 6

The procedure described in Example 5 was repeated using NSD Shower Gel C as hereinbefore described instead of Shower Gel B and using a different deodorant composition.

The formulation of deodorant composition 6 was as follows:

| Deodorant Composition 6 | | | |
|---|---|---|---|
| Components | Parts | Class | Total in class |
| Clove leaf oil | 10.0 | 1 | |
| | | | 11.25 |
| LRG 201 | 1.25 | 1 | |
| Petitgrain oil | 10.0 | 2 | 10.0 |
| p-t-Butyl α-methyl hydro cinnamic aldehyde | 15.0 | 3 | 15.0 |
| 3a-Methyl-dodecyahydro-6,6,9a-trimethylnaphtho-2(2,1-b) furan | 0.5 | 4 | 0.5 |
| o-t-Butylcyclohexyl acetate | 2.0 | 5 | |
| Diethyl phthalate | 9.25 | 5 | 21.25 |
| i-Nonyl acetate | 10.0 | 5 | |
| Phenyl ethyl alcohol | 10.0 | 6 | 10.0 |
| Ingredients | | | |
| Benzyl propionate | 4.0 | | |
| Bergamot oil | 15.0 | | |
| Dimethyl benzyl carbinyl acetate | 5.0 | | |
| iso-Butyl benzoate | 5.0 | | |
| Neroli oil | 3.0 | | |
| | 100.0 | | |

| Total amount of components | 68.0 |
|---|---|
| Number of components present | 9 |
| Average amount of each component | 7.6 |
| Number of classes represented | 6 |

Results of Deodorant Value Test 6 using NSD shower gel

| | Control gel | Test gel |
|---|---|---|

|                | Deodorant Composition 6 | |
|----------------|------------|------|
| Average scores | 3.33 | 1.88 |
| Deodorant value | | 1.45 |

By way of comparison, the Deodorant Value of Deodorant Composition 6 was also determined in the standard 80/20/5 soap bar as described in the Deodorant Value Test.

Results of Deodorant Value Test using 80/20/5 soap base bar

|                | Control bar | Test bar |
|----------------|-------------|----------|
| Average scores | 3.25 | 2.33 |
| Deodorant value | | 0.92 |

As with Example 5, it was apparent that the effect of the deodorant composition was enhanced following use of the NSD shower gel as compared with the standard 80/20/5 soap base.

EXAMPLE 7

The procedure described in Example 1 was repeated using NSD Fabric Washing Liquid C as hereinbefore described instead of Fabric Washing Powder C and using Deodorant Composition 3 as described in Example 3.

The results of Deodorant Value Test 7 (using NSD liquid plus Deodorant Composition 3) were as follows:

|                | Control liquid | Test liquid |
|----------------|----------------|-------------|
| Average scores | 2.64 | 2.14 |
| Deodorant value | | 0.50 |

EXAMPLE 8

The procedure described in Example 1 was repeated using NSD Fabric Washing Powder D as hereinbefore described instead of Fabric Washing Powder C and using Deodorant Composition 2 as described in Example 2.

The results of Deodorant Value Test 8 (using NSD powder plus Deodorant Composition 2) were as follows:

|                | Control powder | Test powder |
|----------------|----------------|-------------|
| Average scores | 2.70 | 1.76 |
| Deodorant value | | 0.94 |

EXAMPLE 9

The procedure described in Example 1 was repeated using NSD Fabric Washing Powder F as hereinbefore described instead of Fabric Washing Powder C and using Deodorant Composition 3 as described in Example 3.

The results of Deodorant Value Test 9 (using NSD powder plus Deodorant Composition 3) were as follows:

|                | Control powder | Test powder |
|----------------|----------------|-------------|
| Average scores | 2.76 | 1.70 |
| Deodorant value | | 1.06 |

APPENDIX

The following glossary provides further information, including the suppliers' names, which will aid identification of some of the aforementioned deodorant components & ingredients.

| Dimyrcetol | Dimyrcetol (IFF) |
|------------|------------------|
| Hercolyn D | Tetrahydro abietate + dihydro abietate (HP) |
| LRG 201 | Oakmoss speciality (RB) |
| Pelargene | Pelargene (PPL) |
| Rose-D-Oxide | Rose oxide synthetic (PPL) |
| Sandalone | Sandalone (PPL) |
| Perfume Houses | |
| HP | Hercules Powder Co. |
| IFF | International Flavour & Fragrances Inc. |
| RB | Roure Bertrand |
| PPL | Proprietary Perfumes Limited |

All materials which are classified by a name and number, such as those having the 'AB' notation, are obtainable from Proprietary Perfumes Limited.

What is claimed is:
1. A deodorant detergent product comprising:
   (i) from 0.5 to 99.99% by weight of a non-soap detergent active compound, and
   (ii) from 0.01 to 10% by weight of a deodorant composition comprising from 45 to 100% by weight of deodorant components, said components having a lipoxidase-inhibiting capacity of at least 50% or a Raoult variance ratio of at least 1.1, said components being classified into six classes consisting of:
   Class 1: phenolic substances
   Class 2: essential oils, extracts, resins and synthetic oils
   Class 3: aldehydes and ketones
   Class 4: polycyclic compounds
   Class 5: esters
   Class 6: alcohols,
provided that where a component can be classified into more than one class, it is placed in the lower or lowest numbered class;
   said components being so selected that
   (a) the deodorant composition contains at least five components of which at least one must be selected from each of class 1, class 2 and class 4;
   (b) the deodorant composition contains components from at least 4 of the 6 classes; and
   (c) any component present in the deodorant composition at a concentration of less than 0.5% by weight of said composition is eliminated from the requirements of (a) and (b) said deodorant composition having a deodorant value of from 0.50 to 3.5 as measured by the Deodorant Value Test.

2. The deodorant detergent product of claim 1 wherein the deodorant composition has a deodorant value of from 0.90 to 3.5 as measured by the Deodorant Value Test.

3. The deodorant detergent product of claim 1 wherein the deodorant composition has a deodorant value of from 1.20 to 3.5 as measured by the Deodorant Value Test.

4. The deodorant detergent product of claim 1 additionally comprising a soap.

5. The deodorant detergent product of claim 1 further comprising a germicide or a zinc salt.

6. The deodorant detergent product of claim 1 wherein the amount of deodorant components present in said class comprising phenolic substances and said class comprising essential oils, extracts, resins and synthetic oils and said class comprising polycyclic compounds, is at least 1% by weight of the deodorant composition for each of said classes, and the amount of deodorant components present in said further class chosen from the remaining three classes is at least 1% by weight of the deodorant composition.

7. The deodorant detergent product of claim 1 wherein the average concentration of all such components present is at least 5% by weight where four of said classes is represented, or at least 4.5% by weight where five or six of said classes is represented.

8. The deodorant detergent product of claim 1 wherein the amount of deodorant components present in said class comprising phenolic substances and said class comprising essential oils, extracts, resins and synthetic oils and said class comprising polycyclic compounds, is at least 3% by weight of the deodorant composition for each of said classes and the amount of deodorant components present in said further class chosen from the remaining three classes is at least 3% by weight of the deodorant composition.

9. The deodorant detergent product of claim 1 wherein at least five of the classes is represented.

10. The deodorant detergent product of claim 1 wherein all six classes are represented.

11. The deodorant detergent product of claim 1 wherein the said deodorant components are chosen from:

Class 1—Phenolic substances iso-Amyl salicylate
Benzyl salicylate
Carvacrol
Clove leaf oil
Ethyl vanillin
iso-Eugenol
LRG 201
Mousse de chene Yugo
Pimento leaf oil
Thyme oil red

Class 2—Essential oils, extracts, resins, "synthetic" oils. (denoted by "AB")

Benzoin Siam resinoids
Bergamot AB 37
Bergamot AB 430
Geranium AB 76
Geranium oil
Opoponax resinoid
Patchouli oil
Petitgrain oil
Pomeransol AB 314

Class 3—Polycyclic compounds

Coumarin
1,3,4,6,7,8-Hexahydro-4,6,6,7,8,9-hexamethylcyclopenta-$\gamma$-2-benzopyran
3a-Methyl-dodecahydro-6,6,9a-trimethylnaphtho(2,1-b)furan
$\beta$-Naphthyl methyl ether

Class 4—Aldehydes and ketones

6-Acetyl-1,1,3,4,4,6-hexamethyltetrahydronaphthalene
p-t-Amyl cyclohexanone
p-t-Butyl-$\alpha$-methyl hydrocinnamic aldehyde
2-n-Heptylcyclopentanone
$\alpha$-iso-Methyl ionone
$\alpha$-Methyl naphthyl ketone

Class 5—Esters o-t-butylcyclohexyl acetate
p-t-Butylcyclohexyl acetate
Diethyl phthalate
Nonanediol-1,3-diacetate
Nonanolide-1:4
i-Nonyl acetate
i-Nonyl formate

Class 6—Alcohols

Dimyrcretol
Phenylethyl alcohol
Tetrahydromuguol

12. A process for preparing the deodorant detergent product of claim 1 which comprises mixing the non-soap detergent-active compound with the deodorant composition to provide a deodorant detergent product, said product comprising from 0.5 to 99.99% by weight of the non-soap detergent active compound and from 0.01 to 10% by weight of the deodorant composition.

13. A method for suppressing human body malodour which comprises applying to the skin in the region of apocrine sweat glands the deodorant detergent product of claim 1.

14. A method for suppressing human body malodour which comprises contacting the skin in the region of apocrine sweat glands with a fabric treated with the deodorant detergent product of claim 1.

* * * * *

UNITED STATES PATENT AND TRADEMARK OFFICE
CERTIFICATE OF CORRECTION

PATENT NO. : 4,304,679

DATED : December 8, 1981

INVENTOR(S) : Hooper et al

Page 1 of 2

It is certified that error appears in the above—identified patent and that said Letters Patent is hereby corrected as shown below:

Claim 11 - Column 28, line 8 to line 15, please change:

"Class 3 — Polycyclic compounds
    Coumarin
    1,3,4,6,7,8-Hexahydro-4,6,6,7,8,9-hexamethylcy-
      clopenta-γ-2-benzopyran
    3a-Methyl-dodecahydro-6,6,9a-trimethylnaph-
      tho(2,1-b)furan
    β-Naphthyl methyl ether"

to

--Class 3 — Aldehydes and ketones
    6-Acetyl-1,1,3,4,4,6-hexamethyltetrahydronaphtha-
      lene
    p-t-Amyl cyclohexanone
    p-t-Butyl-α-methyl hydrocinnamic aldehyde
    2-n-Heptylcyclopentanone
  α-iso-Methyl ionone
  α-Methyl naphthyl ketone

UNITED STATES PATENT AND TRADEMARK OFFICE
CERTIFICATE OF CORRECTION

PATENT NO. : 4,304,679

DATED : December 8, 1981

INVENTOR(S) : Hooper et al

It is certified that error appears in the above—identified patent and that said Letters Patent is hereby corrected as shown below:

Claim 11 - Column 28, lines 16-24, please change:

"Class 4 — Aldehydes and ketones
    6-Acetyl-1,1,3,4,4,6-hexamethyltetrahydronaphthalene
    p-t-Amyl cyclohexanone
    p-t-Butyl- $\alpha$-methyl hydrocinnamic aldehyde
    2-n-Heptylcyclopentanone
    $\alpha$-iso-Methyl ionone
    $\alpha$-Methyl naphthyl ketone"

to

--Class 4 — Polycyclic Compounds 1,3,4,6,7,8-Hexahydro-4,6,6,7,8,9-hexamethylcyclopenta-$\gamma$-2-benzopyran
    3a-Methyl-dodecahydro-6,6,9a-trimethylnaphtho(2,1-b)furan
    $\beta$-Naphthyl methyl ether--

Signed and Sealed this

Seventh Day of September 1982

[SEAL]

Attest:

Attesting Officer

GERALD J. MOSSINGHOFF

Commissioner of Patents and Trademarks